United States Patent [19]
Wu et al.

[11] Patent Number: 6,030,954
[45] Date of Patent: Feb. 29, 2000

[54] TARGETED DELIVERY OF POLY- OR OLIGONUCLEOTIDES TO CELLS

[75] Inventors: George Y. Wu; Catherine H. Wu, both of Bloomfield, Conn.

[73] Assignee: University of Connecticut, Storrs, Conn.

[21] Appl. No.: 08/458,633

[22] Filed: Jun. 2, 1995

Related U.S. Application Data

[63] Continuation of application No. 07/941,368, Sep. 4, 1992, abandoned, which is a continuation-in-part of application No. 07/864,003, Apr. 3, 1992, abandoned, which is a continuation-in-part of application No. 07/788,119, Nov. 4, 1991, abandoned, which is a continuation-in-part of application No. 07/755,083, Sep. 5, 1991, abandoned.

[51] Int. Cl.[7] .................................................. A61K 48/00
[52] U.S. Cl. ........................... 514/44; 435/6; 435/320.1; 435/455; 536/23.1; 536/23.72; 536/24.5
[58] Field of Search .......................... 514/44; 435/172.3, 435/455, 320.1, 325, 6; 935/34, 36, 78; 562/23.1

[56] References Cited

U.S. PATENT DOCUMENTS

| | | | |
|---|---|---|---|
| 4,987,071 | 1/1991 | Cech | 435/91 |
| 5,166,320 | 11/1992 | Wu | 530/395 |
| 5,190,931 | 3/1993 | Inouge | 435/91 |
| 5,264,562 | 11/1993 | Matteucci | 536/23.1 |
| 5,610,050 | 3/1997 | Blum et al. | 435/238 |
| 5,677,439 | 10/1997 | Weiss et al. | 536/23.1 |
| 5,792,645 | 8/1998 | Beug et al. | 435/455 |

FOREIGN PATENT DOCUMENTS

| | | |
|---|---|---|
| 2012311 | 9/1990 | Canada. |
| 331 939 | 9/1989 | European Pat. Off. . |
| WO 91/04753 | 4/1991 | WIPO . |

OTHER PUBLICATIONS

Paronetto, F. et al., "Woodchuck Hepatitis Virus Infection: A Model of Human Hepatic Diseases and Hepatocellular Carcinoma", *Progress in Liver Diseases*, vol. 9, pp. 463–483, 1990.
Kenji, A. et al., "Localization of Woodchuck Hepatitis Virus in the Liver", *Hepatology*, vol. 8, No. 1, pp. 88–92, 1988.
Hantz, O. et al., "Comparison of Properties of Woodchuck Hepatitis Virus and Human Hepatitis B Virus Endogenous DNA Polymerases", *Antimicrobial Agents and Chemotherapy*, vol. 25, No. 2, pp. 242–246, 1984.
Schwartz. A.L. et al., "The Hepatic Asialoglycoprotein Receptor", *CRC Critical Reviews in Biochemistry*, vol. 16, Issue 3 pp. 207–233, 1984.
Supplementary Partial European Search Report issued during prosecution of EP 92 92 0863 and dated Aug. 3, 1994.
Wu, G. and Wu, C., (1991) "Delivery Systems for Gene Therapy", *Biotherapy*, vol. 3, No. 1, pp. 87–96.
Rothenberg, M., et al., (1989) "Oligodeoxynucleotides as Anti–Sense Inhibitors of Gene Expression: Therapeutic Implications",*Journal of the National Cancer Institute*, vol. 81, No. 20, pp. 39–44.
Wagner, E. et al., *Proc. Natl. Acad. Sci.* USA 87:3410–3414 (1990).
Wu, C.H. et al., *J. of Biol. Chem.* 264(29):16987 (1989).
International Search Report, PCT/US92/07339, Dec. 1992.
Wu, G.Y. and Wu, C.H., *J. Biol. Chem.* 262(10):4429–4432 (1987).
Zenke, M. et al., *Proc. Natl. Acad. Sci.* USA 87:3655–3659 (1990).
Crystal (Science, vol. 270, 1995, p. 404–410).
Kreitman et al., (P.N.A.S., vol. 91, pp. 6889–6893, 1994).
Stein et al. (Mol. Cell Biol. 14(5):3392–3402, 1994).
Wu et al. (J. Biological Chemistry, vol. 263, 1988, pp. 14621–14624).
Huckett et al., Chemical Pharmacology, vol. 40, 2:253–263, 1990.
Mascotti et al., PNAS, vol. 87, 2142–2146, 1990.
Stull et al Pharmaceut. Res.,12(4): 465, 1995.
Gura Science 270: 575, 1995.
Barinaga, Science, 262: 1512, 1993.
Uhlmann, Chemical Review, vol. 90, 4, 1990.
Lemaitre et al. PNAS 84: 648, 1987.
Wu et al JBC 263(29): 14621, 1988.
Hirschman PNAS 77(9): 5507, 1980.

*Primary Examiner*—Scott D. Priebe
*Assistant Examiner*—Dave Trong Nguyen
*Attorney, Agent, or Firm*—Lahive & Cockfield, LLP; Jane E. Remillard, Esq.; Giulio A. DeConti, Jr., Esq.

[57] ABSTRACT

Molecular complexes for targeting oligonucleotides, such as antisense oligonucleotides or ribozymes, to a specific cell to block expression of a gene or genes in the cell are described. The single-stranded poly- or oligonucleotide is complexed to a conjugate of a cell-specific binding agent and a poly- or oligonucleotide-binding agent. The cell-specific binding agent is specific for a cellular surface structure which mediates internalization of the complex. An example is the asialoglycoprotein receptor of hepatocytes. The poly- or oligodeoxy-nucleotide-binding agent is a compound such as a polycationic protein which stably complexes the oligonucleotide under extracellular conditions and releases it under intracellular conditions so that it can hybridize with the target RNA. The molecular complex is stable and soluble in physiological fluids and can be used to selectively introduce antisense oligonucleotides, ribozymes or other single-stranded oligonucleotides into a cell to inhibit expression of a gene within the cell. The oligonucleotide can be directed against cellular genes (e.g., cellular oncogenes) or genes of noncellular origin (e.g., viral oncogenes, genes of an infecting pathogen).

25 Claims, 3 Drawing Sheets

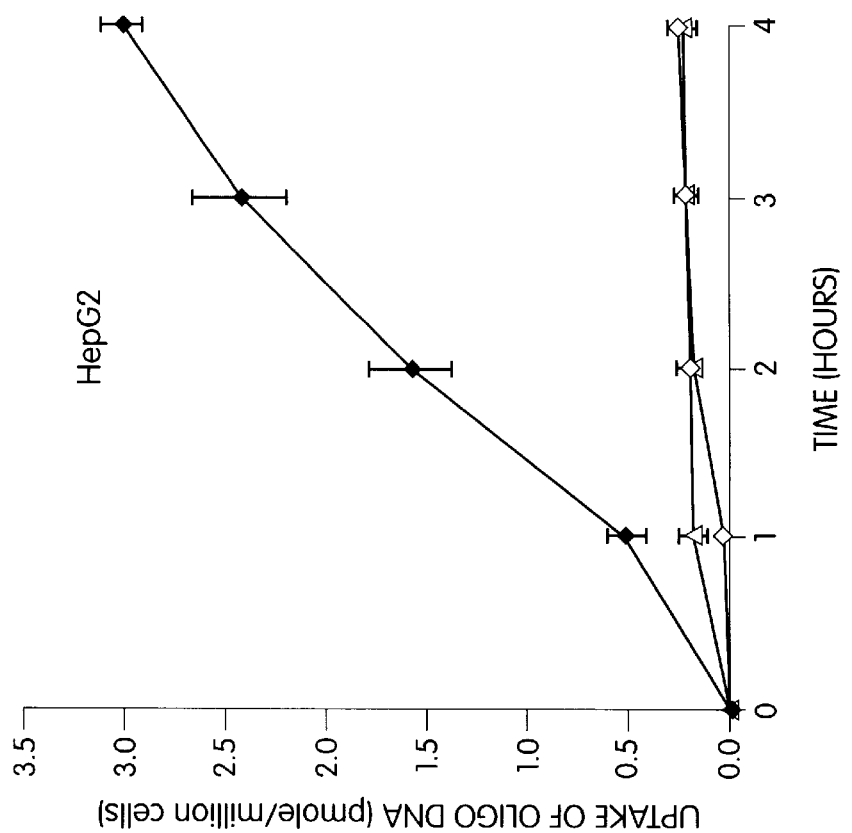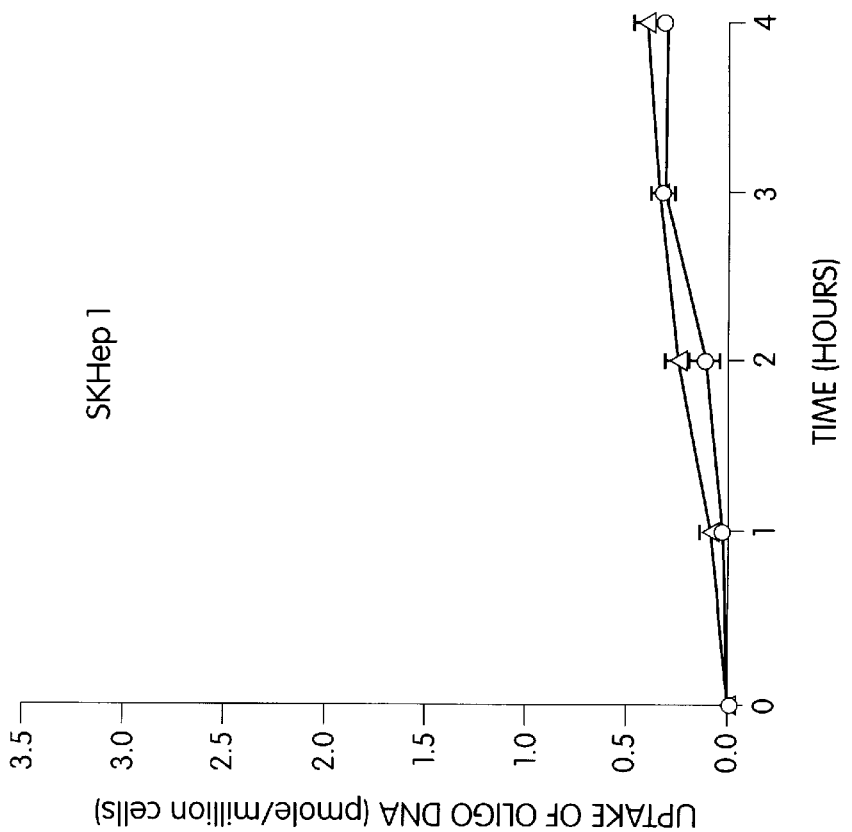

TARGETED DELIVERY OF POLY- OR OLIGONUCLEOTIDES TO CELLS

This application is a continuation of U.S. application Ser. No. 07/941,368, filed Sep. 4, 1992, which is a continuation-in-part of U.S. application Ser. No. 07/864,003, filed Apr. 3, 1992, which is a continuation-in-part of U.S. application Ser. No. 07/788,119, filed Nov. 4, 1991, now abandoned. U.S. application Ser. No. 07/788,119 is a continuation-in-part of U.S. Ser. No. 07/755,083, filed Sep. 5, 1991, now abandoned.

GOVERNMENT SUPPORT

The work leading to this invention was supported, in part, by research grants from the United States government.

BACKGROUND OF THE INVENTION

Antisense oligonucleotides hold great promise as means of specifically inhibiting unwanted gene expression in cells. Improvements in the delivery of oligonucleotides to cells will enhance effectiveness. Naked antisense oligonucleotides can be taken up by cells non-specifically and at low efficiency. Some methods have been explored to increase uptake. Lemaitre et al. covalently coupled an oligonucleotide to polylysine and demonstrated inhibition of viral gene expression at several fold lower than DNA concentrations compared to mixtures of polylysine and antisense DNA (Lemaitre, M. et al. *Proc. Natl. Acad. Sci. USA* 84:648–652). Although specific antiviral effects were shown, specific delivery was not demonstrated.

SUMMARY OF THE INVENTION

This invention pertains to a soluble, targetable molecular complex for targeting poly- or oligonucleotides to a specific cell to inhibit the expression of a gene or genes. The molecular complex comprises a single-stranded poly- or oligonucleotide which hybridizes to an RNA transcript of the gene, complexed to a carrier which is a conjugate of a cell-specific binding agent and a poly- or oligonucleotide-binding agent. The complex is administered in a pharmaceutically acceptable solution in an amount sufficient to hybridize to and inhibit the function of the RNA transcript.

The poly- or oligonucleotide can be DNA or RNA. For antisense applications, an antisense oligodeoxy-nucleotide can be used which hybridizes to and inhibits the function of an RNA. The targeted RNA is typically a messenger RNA. The oligonucleotide can also be an RNA which has catalytic activity (a ribozyme). The target for antisense or ribozyme-mediated inhibition can be a gene or genes of cellular origin (e.g., a cellular oncogene) or of noncellular origin (e.g., a viral oncogene or the genes of an infecting pathogen such as a virus).

The cell-specific binding agent is specific for a cellular surface structure, typically a receptor, which mediates internalization of bound ligands by endocytosis, such as the asialoglycoprotein receptor of hepatocytes. The cell-specific binding agent can be a natural or synthetic ligand (for example, a protein, polypeptide, glycoprotein, carbohydrate, etc.) or it can be an antibody, or an analogue thereof, which specifically binds a cellular surface structure which then mediates internalization of the bound complex. The poly- or oligonucleotide-binding component of the conjugate is a compound such as a polycation which stably complexes the single-stranded poly- or oligonucleotide under extracellular conditions and releases it under intracellular conditions so that it can function within the cell.

The complex of the gene and the carrier can be used in vitro or in vivo to selectively deliver poly- or oligonucleotides to target cells. The complex is stable and soluble in physiological fluids. It can be administered in vivo where it is selectively taken up by the target cell via the surface-structure-mediated endocytotic pathway. The incorporated poly- or oligonucleotide hybridizes with its complementary RNA, thereby inhibiting function of the RNA and expression of the target gene or genes.

BRIEF DESCRIPTION OF THE FIGURES

FIG. 1 shows the uptake of complexed antisense DNA by HepG2 and SK Hep1 cells.

DETAILED DESCRIPTION OF THE INVENTION

Figure 2:
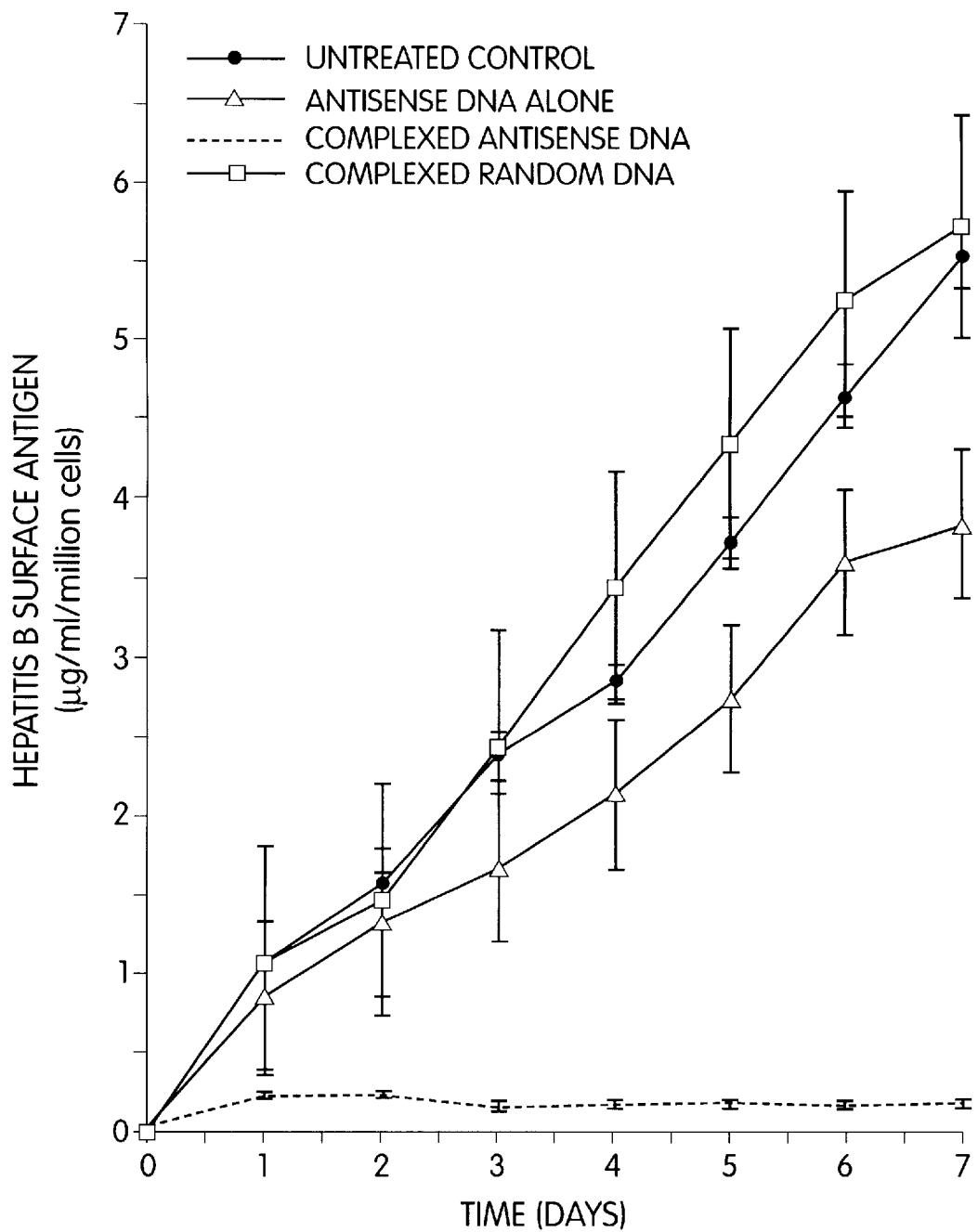
FIG. 2 shows the effect of complexed antisense DNA on hepatitis B virus surface antigen concentration in culture medium.

A soluble, targetable molecular complex is used to selectively deliver a single-stranded poly- or oligonucleotide to a target cell or tissue in vivo to specifically inhibit gene expression. The molecular complex comprises the oligonucleotide to be delivered complexed to a carrier made up of a binding agent specific for the target cell and a DNA-binding agent. The complex is selectively taken up by the target cell and the oligonucleotide hybridizes to the RNA transcript which inhibits expression of the targeted gene(s).

The poly- or oligonucleotide is a single-stranded molecule which hybridizes to a specific RNA under intracellular conditions. The degree of complementarity required for appropriately specific hybridization to the target RNA sequence under intra-cellular conditions can be determined empirically.

In a preferred embodiment, the oligonucleotide is an antisense oligodeoxynucleotide. The antisense oligodeoxynucleotide can be a normal oligodeoxy-nucleotide or an analogue of an oligodeoxynucleotide (e.g., phosphorothioate oligonucleotides, in which one of the phosphate oxygens is replaced by a sulfur atom) sufficiently stable to reach the target in effective concentrations. See e.g., Stein, C. A. and Cohen, J. S. (1988) *Cancer Research* 48:2659–2668. Antisense oligodeoxynucleotides can be prepared by standard synthetic procedures.

The antisense oligonucleotides can be designed to operate by different mechanisms of gene inhibition. Generally, these mechanisms involve the hybridization of the oligonucleotide to a specific RNA sequence, typically a messenger RNA. The targeted sequence can be located in the coding region of the RNA or it can be a signal sequence required for processing or translation of the RNA. The targeted sequence can be a sequence normally found in an organism or a sequence found in a pathogenic organism but not in its host. Alternatively, the oligonucleotide may form a triple helix DNA structure, inhibiting transcription of the mRNA sequence.

In other embodiments, the oligonucleotide can be an RNA molecule which has catalytic activity, i.e., a ribozyme. Ribozymes are advantageous because they specifically cleave and, thus, destroy the targeted RNA sequence. Ribozymes are described in U.S. Pat. No. 4,987,071.

The carrier component of the complex is a conjugate of a cell-specific binding agent and an oligonucleotide-binding agent. The cell-specific binding agent specifically binds a cellular surface structure which mediates its internalization by, for example, the process of endocytosis. The surface structure can be a protein, polypeptide, carbohydrate, lipid or combination thereof. It is typically a surface receptor which mediates endo-cytosis of a ligand. Thus, the binding agent can be a natural or synthetic ligand which binds the receptor. The ligand can be a protein, polypeptide, carbohydrate, lipid or a combination thereof which has functional groups that are exposed sufficiently to be recognized by the cell surface structure. It can also be a component of a biological organism such as a virus, cells (e.g., mammalian, bacterial, protozoan) or artificial carriers such as liposomes.

The binding agent can also be an antibody, or an analogue of an antibody such as a single chain antibody, which binds the cell surface structure.

Ligands useful in forming the carrier will vary according to the particular cell to be targeted. For targeting hepatocytes, glycoproteins having exposed terminal carbohydrate groups such as asialoglycoprotein (galactose-terminal) can be used, although other ligands such as polypeptide hormones may also be employed. Examples of asialoglycoproteins include asialoorosomucoid, asialofetuin and desialylated vesicular stomatitis virus. Such ligands can be formed by chemical or enzymatic desialylation of glycoproteins that possess terminal sialic acid and penultimate galactose residues. Alternatively, asialoglycoprotein ligands can be formed by coupling galactose terminal carbohydrates such as lactose or arabinogalactan to non-galactose bearing proteins by reductive lactosamination.

For targeting the molecular complex to other cell surface receptors, other types of ligands can be used, such as mannose for macrophages (lymphoma), mannose-6-phosphate glycoproteins for fibroblasts (fibrosarcoma), intrinsic factor-vitamin B12 for enterocytes and insulin for fat cells. Alternatively, the cell-specific binding agent can be a receptor or receptor-like molecule, such as an antibody which binds a ligand (e.g., antigen) on the cell surface. Such antibodies can be produced by standard procedures.

The poly- or oligonucleotide-binding agent complexes the oligonucleotide to be delivered. Complexation with the oligonucleotide must be sufficiently stable in vivo to prevent significant uncoupling of the oligonucleotide extracellularly prior to internalization by the target cell. However, the complex is cleavable under appropriate conditions within the cell so that the oligonucleotide is released in functional, hybridizable form. For example, the complex can be labile in the acidic and enzyme rich environment of lysosomes. A non-covalent bond based on electrostatic attraction between the binding agent and the oligonucleotide provides extracellular stability and is releasable under intracellular conditions.

Preferred poly- or oligonucleotide-binding agents are polycations that bind the negatively charged nucleic acid strands. These positively charged materials can bind noncovalently with the poly- or oligonucleotide to form a soluble, targetable molecular complex which is stable extracellularly but which releases the poly- or oligonucleotide as a functional (e.g., hybridizable) molecule intracellularly. Suitable polycations are polylysine, polyarginine, polyornithine, basic proteins such as histones, avidin, protamines and the like. A preferred polycation is polylysine (e.g., ranging from 3,800 to 60,000 daltons). Other noncovalent bonds that can be used to releasably link the poly- or oligonucleotide include hydrogen bonding, hydrophobic bonding, electrostatic bonding alone or in combination such as, anti-poly- or oligonucleotide antibodies bound to poly- or oligonucleotide, and streptavidin or avidin binding to poly- or oligonucleotide containing biotinylated nucleotides.

The carrier can be formed by chemically linking the cell-specific binding agent and the oligonucleotide-binding agent. The linkage is typically covalent. A preferred linkage is a peptide bond. This can be formed with a water soluble carbodiimide as described by Jung, G. et al. (1981) *Biochem. Biophys. Res. Commun.* 101:599–606. An alternative linkage is a disulfide bond.

The linkage reaction can be optimized for the particular cell-specific binding agent and oligonucleotide-binding agent used to form the carrier. Reaction conditions can be designed to maximize linkage formation but to minimize the formation of aggregates of the carrier components. The optimal ratio of cell-specific binding agent to poly- or oligonucleotide-binding agent can be determined empirically. When polycations are used, the molar ratio of the components will vary with the size of the polycation and the size of the poly- or oligonucleotide. For example, for a conjugate of asialoorosomucoid linked to polylysine complexed with a 21-mer oligonucleotide the ratio can range from 2:1 to 1:2 by weight (asialoorosomucoid:oligonucleotide) can be used. Uncoupled components and aggregates can be separated from the carrier by molecular sieve or ion exchange chromatography. In a preferred embodiment, the conjugate is purified on a high pressure liquid cation exchange column (Aquapore™ cation-exchange, Rainin) with stepwise elution with 0.1 M sodium acetate, pH 5.0, 2.5, 2.25 and 2.0.

To form the complex, the poly- or oligonucleotide and carrier are mixed and incubated under conditions conducive to complexation. For example, the poly- or oligonucleotide and carrier can be mixed at the appropriate ratio in 2 M NaCl and the solution can be diluted to 0.15 M and filtered to provide an administrable composition.

The molecular complex can contain more than one copy of the nucleic acid strand. The amount of poly- or oligonucleotide, of course, should not exceed that required to maintain solubility of the resulting complex. The preferred weight or molar ratio of carrier to poly- or oligonucleotide for the construct employed can be determined by routine experimentation.

The molecular complex of this invention can be administered parenterally. Preferably, it is injected intravenously. The complex is administered in solution in a physiologically acceptable vehicle.

The molecular complex of this invention can be used to target delivery of a wide range of poly- and oligonucleotide for specific hybridization usually to an RNA target. The target can also be DNA by triplex formation. Duvall-Valentine et al. (1992) *PNAS* 89:504–508. In the former case, depending on the therapeutic goal, the oligonucleotide can be directed against translation of a gene or genes of cellular origin (e.g., a cellular oncogene) or of noncellular origin (e.g., a viral oncogene or the genes of an infecting pathogen such as a virus or a parasite such as malaria, trypanosome, lysteria or mycoplasma). In the latter cases, the antisense can be directed against transcription of target genes.

In one embodiment, the method of this invention can be used to treat hepatitis infection. The complex can be used to deliver an antisense oligodeoxynucleotide specifically to liver cells to block production of hepatitis virus. One strategy is to take advantage of the fact that, because of its compact nature, the human hepatitis B virus has only one polyadenylation signal (nucleotides 1903–1923). The signal is common to all hepatitis B viral-derived mRNA and is different from the mammalian signal. As a result, antisense oligodeoxynucleotides complementary to this region can block viral protein synthesis. In a preferred embodiment, the antisense strand is complexed to a carrier comprising a ligand for the hepatic asialoglycoprotein receptor and a polycationic protein such as polylysine to provide a soluble molecular complex targetable to the liver.

In another embodiment, the method of this invention can be used to alter the expression of a gene of cellular origin. This method may be useful in the treatment of diseases characterized by abnormal biosynthesis, especially overexpression, of normal or abnormal cellular proteins.

This invention is illustrated further by the following examples.

EXAMPLE 1

MATERIALS AND METHODS
Cells and Cell Culture

Human hepatoma, HepG2 2.2.15 cells kindly provided by Dr. George Acs (Mt. Sinai School of Medicine, NY) and SK Hep1 cells were grown in DMEM and 10% fetal calf serum as described previously (Wu, G. Y. and Wu, C. H. (1987) *J. Biol. Chem.* 262:4429–4432).

Preparation of Targetable Antisense DNA

A targetable, soluble DNA carrier was prepared by coupling asialoorosomucoid to poly L-lysine (Sigma) ($M_r$=59,000) using 1-ethyl-3-(3-dimethyl-aminopropyl) carbodiimide) (Pierce) as described previously (Wu, G. Y. and Wu, C. H. (1987) *J. Biol. Chem.* 262:4429–4432) except that the conjugate was purified by cation exchange chromatography using a high pressure liquid chromatographic system (Rainin) employing an Aquapore C-300 column (Rainin) and stepwise elution with 0.1 M sodium acetate, pH 5.0, 2.5, 2.25 and 2.0. The second peak eluted from the column, as detected by U.V. absorption at 230 nm, was determined to be the optimal conjugate form and was used for all subsequent experiments. A 21-mer oligodeoxynucleotide, complementary to a portion of the human hepatitis B virus (ayw subtype) (Hirschman, S. Z. et al. (1980) *Proc. Natl. Acad. Sci. USA* 77:5507–5511) including the polyadenylation signal, corresponding to nucleotides 1903–1923 (See SEQUENCE ID NO. 1-TTTATAAGGGTCGATGTCCAT) of the viral genome, was synthesized with phosphorothioate linkages on an automated nucleotide synthesizer (Applied Biosystems) (Matsukura, M. et al. (1987) *Proc. Natl. Acad. Sci, USA* 84:7705–7710). As a control, a random 21-mer sequence was prepared in an identical fashion. The purity of oligonucleotides was determined by electrophoresis through 15% polyacrylamide gels stained with ethidium bromide. Antisense DNA was titrated with conjugate to form a soluble complex using an agarose gel retardation system as described previously (Wu, G. Y. and Wu, C. H. (1987) *J. Biol. Chem.* 262:4429–4432) and a conjugate to DNA ratio of 1.6:1 by weight (asialoorosomucoid: DNA) was selected.

Assay for Receptor-Mediated Uptake of Complexed Antisense DNA

To evaluate uptake of oligonucleotides, antisense DNA was end-labeled with $^{32}P$ (Sambrook, J. et al. (1989) *Molecular Cloning—A Laboratory Manual*, Cold Spring Harbor Laboratory, 2nd ed., vol. 2, pg. 11.31). DNA alone, or in the form of a complex was added to medium of HepG2 and SK Hep1 cells to make 50 $\mu$M solutions with respect to added antisense DNA. Uptake was determined as described previously for asialoglycoproteins (Schwartz, A. L. et al. (1981) *J. Biol. Chem.* 256:8878–8881). In brief, cells were incubated with ligands at 37° C. and at regular time intervals, dishes were chilled to 4° C., washed with cold 10 mM EDTA-phosphate buffered saline and the cell layers removed and scintillation counted. To determine counts bound to the cell surface, identical sets of cells were incubated at 4° C. with ligands and, after washing as described above, the cell layers were removed and adherent radioactivity was determined by scintillation counting. Uptake was calculated as the difference between total cell-associated counts at 37° C. and counts bound to the cells at 4° C. for each time point. All points were determined in triplicate and results shown as means±SEM expressed as pmole DNA/$10^6$ cells.

Antisense DNA and Viral Gene Expression

To determine the effect of antisense DNA on viral gene expression, HepG2 2.2.15 cells were seeded six days pre-confluence and incubated at 37° C. in medium containing antisense DNA alone, complexed antisense DNA, complexed random DNA, or medium alone. All media containing added DNA were initially 50 $\mu$M with respect to DNA. At daily intervals, 50 $\mu$l of medium was sampled and assayed for hepatitis B surface antigen by an ELISA (Abbott) method as described by the manufacturer, modified for quantitation using serially diluted standard surface antigen (CalBiochem) which produced a linear response within the range of antigen levels found in the samples. Cell number was determined by microscopic counting cells stained with trypan blue. All points were determined in triplicate and the results of four experiments are shown as means±SEM expressed as $\mu$g/ml/$10^6$ cells.

Effect of Antisense DNA on Protein Secretion

HepG2 2.2.15 cells were incubated with 50 $\mu$M complexed DNA as described in FIG. 2 except that 10 $\mu$Ci [$^{35}S$]-methionine (Amersham), specific activity 1000 Ci/mmole, was added to label newly synthesized proteins. After 24 hrs, medium was moved, cells washed with phosphate buffered saline and lysed with 1% sodium dodecyl sulfate which was subsequently removed with triton X-100. Both media and cell lysates were treated with a specific rabbit antisurface antigen antibody (DAKO) and precipitated with protein-A sepharose (Sigma). Precipitates were scintillation counted and each point assayed in triplicate. Total cell protein was determined by colorimetric assay (Bio-Rad). The results of three experiments are shown as means±SEM expressed as cpm/mg cell protein.

In order to assess the effect of complexed antisense DNA on total protein synthesis, cells treated with complexed DNA and labeled with [$^{35}S$]-methionine as described above were separated from media. Total protein was precipitated with 10% trichloroacetic acid and counted. The results of triplicate assays of three experiments are shown as means±SEM expressed as cpm/mg cell protein.

Effect of Antisense DNA on Production of Viral DNA

Cells were incubated with 50 $\mu$M antisense DNA alone, or in the form of complexes. After 24 hrs, medium was removed and HBV DNA, extracted from the medium according to the method of Sells et al. (Sells, M. A. et al. (1987) *Proc. Natl. Acad. Sci. USA* 84:1005–1009) and from the cell layer according to the method of Hirt (Hirt, B. J. (1967) *Mol. Biol.* 26:365–371). Total cell protein was determined by colorimetric assay (Bio-Rad). DNA extracted from equal volumes (40 ml) of medium and from approximately equal numbers of cells ($10^7$) were applied on an agarose gel. HBV DNA was identified by Southern blot using an EcoRI- BglII fragment of the HBV genome (nucleotide 0 to 1982) as a probe labeled with $^{32}$P and exposed to x-ray film as described previously (Sambrook, J. et al. (1989) *Molecular Cloning—A Laboratory Manual*, Cold Spring Harbor Laboratory, 2nd ed., vol. 2, pp. 10.14–10.15). Relative quantitation was achieved by densitometry and confirmed by scintillation counting of corresponding bands.

The first objective was to determine whether a single-stranded DNA oligonucleotide could be bound by an asialoglycoprotein-based carrier and whether it could be specifically targeted to asialoglycoprotein receptor-bearing cells.

FIG. 1 shows uptake of complexed antisense DNA by HepG2 and SK Hep1 cells. A targetable, soluble DNA carrier was prepared by coupling asialoorosomucoid to poly L-lysine using a water soluble carbodiimide as described previously (Wu, G. Y. and Wu, C. H. (1987) *J. Biol. Chem.* 262:4429–4432) and purified as described in Materials and Methods. The conjugate was complexed to a 21-mer oligodeoxynucleotide, complementary to a portion of the human hepatitis B virus including the polyadenylation signal and labeled with $^{32}$P. DNA alone, or in the form of a complex was added to medium to make it 50 μM with respect to added antisense DNA. Uptake was determined as described previously for asialoglycoproteins (Schwartz, A. L. et al. (1981) *J. Biol. Chem.* 256:8878–8881). Cells were incubated at 37° C. and at regular time intervals, dishes were chilled, washed with 10 mM EDTA-phosphate buffered saline. To determine counts bound to the cell surface, identical sets of cells were also incubated at 4° C. with ligands and, after washing as described above, the cell layers were removed and radioactivity determined by scintillation counting. Uptake was calculated as the difference between cell-associated counts at 37° C. and counts bound to the cell surface at 4° C. for each time point. All points were determined in triplicate and results shown as means±SEM expressed as pmole DNA/$10^6$ cells, (o), antisense DNA alone; (♦), complexed antisense DNA; (Δ), complexed antisense DNA plus a 100-fold molar excess of asialoorosomucoid. FIG. 1 shows that in SK Hep1 [asialoglycoprotein receptor (−) cells], the average uptake of antisense DNA alone was less than 0.05 pmole/hr/million cells over 4 hrs of exposure. Incubation with DNA in the form of a complex did not improve the uptake in these cells. Similarly, uptake of antisense DNA alone by HepG2 [asialoglycoprotein receptor (+)] cells was as low as observed in receptor (−) cells over the course of the 4 hrs. However, in the receptor (+) cells, complexed antisense DNA was taken up nearly linearly at an average rate 12 times faster than antisense DNA alone through the 4 hrs of incubation. Accumulation of complexed antisense was also 12 times greater than antisense DNA alone after 4 hrs of exposure. The uptake of complexed DNA was virtually completely blocked by administration of a large molar excess of free carrier protein, asialoorosomucoid, to compete for receptor binding. This confirmed the involvement of asialoglycoprotein receptors in the differential delivery of the antisense DNA.

To determine whether the targeted antisense DNA was functional, effects on hepatitis B viral gene expression were evaluated. FIG. 2 shows the effect of complexed antisense DNA on hepatitis B virus surface antigen concentration in culture medium. HepG2 2.2.15 cells were incubated at 37° C. in medium containing antisense DNA alone, complexed antisense DNA, complexed random DNA, or medium alone. All media containing added DNA were initially 50 μM with respect to DNA. At daily intervals, medium was sampled and assayed for the presence of hepatitis B surface antigen by an ELISA (Abbott) method as described by the manufacturer, modified as described in Materials and Methods. Cell number was determined by microscopically counting cells stained with trypan blue. All points were determined in triplicate and the results of four experiments are shown as means±SEM expressed as μg/ml/$10^6$ cells.

FIG. 2 shows that in untreated control cells, hepatitis B viral surface antigen steadily increased in concentration in their media, rising from 1 μg/ml/$10^6$ cells on the first day to 5.5 μg/ml/$10^6$ cells by the seventh day. Exposure of cells to antisense DNA alone had no significant effect until the 3rd day at which time surface antigen concentration was 30% lower than untreated controls. Nevertheless, surface antigen concentrations in the presence of antisense DNA alone continued to rise steadily throughout the 7 days of exposure. However, treatment with complexed antisense DNA resulted in an 80% inhibition after the 1st day and 95% inhibition by the 7th day compared to untreated controls. There was no significant increase in surface antigen concentration after the first 24 hrs. Complexed random DNA of the same size had no effect on antigen concentrations at any time point under identical conditions.

The lack of accumulation of hepatitis B surface antigen in the medium of cells treated with complexed antisense DNA could have been due to a block in protein secretion. To examine this possibility, the synthesis of new surface antigen was measured in the media and cell layers. Table 1A shows that radiolabeled immunoprecipitable surface antigen in both the medium and cells after treatment with complexed antisense DNA for 24 hrs were decreased to an equal extent (80%) compared to untreated cells. There was no significant intracellular accumulation of newly synthesized antigen that would have been expected if a block in protein secretion had occurred.

Table 1B shows that neither complexed antisense DNA nor random DNA had a significant effect on total newly synthesized protein in the cell layer. A small, 2%, decrease was detected in newly synthesized secreted protein in cells exposed to complexed antisense DNA. This likely reflects the contribution of the inhibition of viral surface antigen synthesis noted in Table 1A. The data, overall, indicate that the observed inhibition of hepatitis B surface antigen synthesis by complexed antisense DNA was specific and could not have been due to a generalized inhibition of total protein synthesis.

TABLE 1A

Immunoprecipitable Hepatitis B Surface Antigen*

| Treatment | Cell Layer+ | Cell Medium+ |
|---|---|---|
| Untreated Control | 56,100 ± 2,321 | 114,500 ± 2,442 |
| Complexed Antisense DNA | 10,200 ± 1,009 | 15,300 ± 890 |
| Complexed Random DNA | 52,500 ± 4,534 | 122,220 ± 5,742 |

TABLE 1B

Total TCA Precipitable Radioactivity*

| Treatment | Cell Layer+ | Cell Medium+ |
|---|---|---|
| Untreated Control | 184,498 ± 2,258 | 712,498 ± 5,435 |
| Complexed Antisense DNA | 188,844 ± 6,240 | 684,302 ± 9,678 |
| Complexed Random DNA | 183,591 ± 5,444 | 706,240 ± 7,544 |

*after 24 hrs incubation
+cpm/mg cell protein
TCA - trichloroacetic acid

Figure 3:
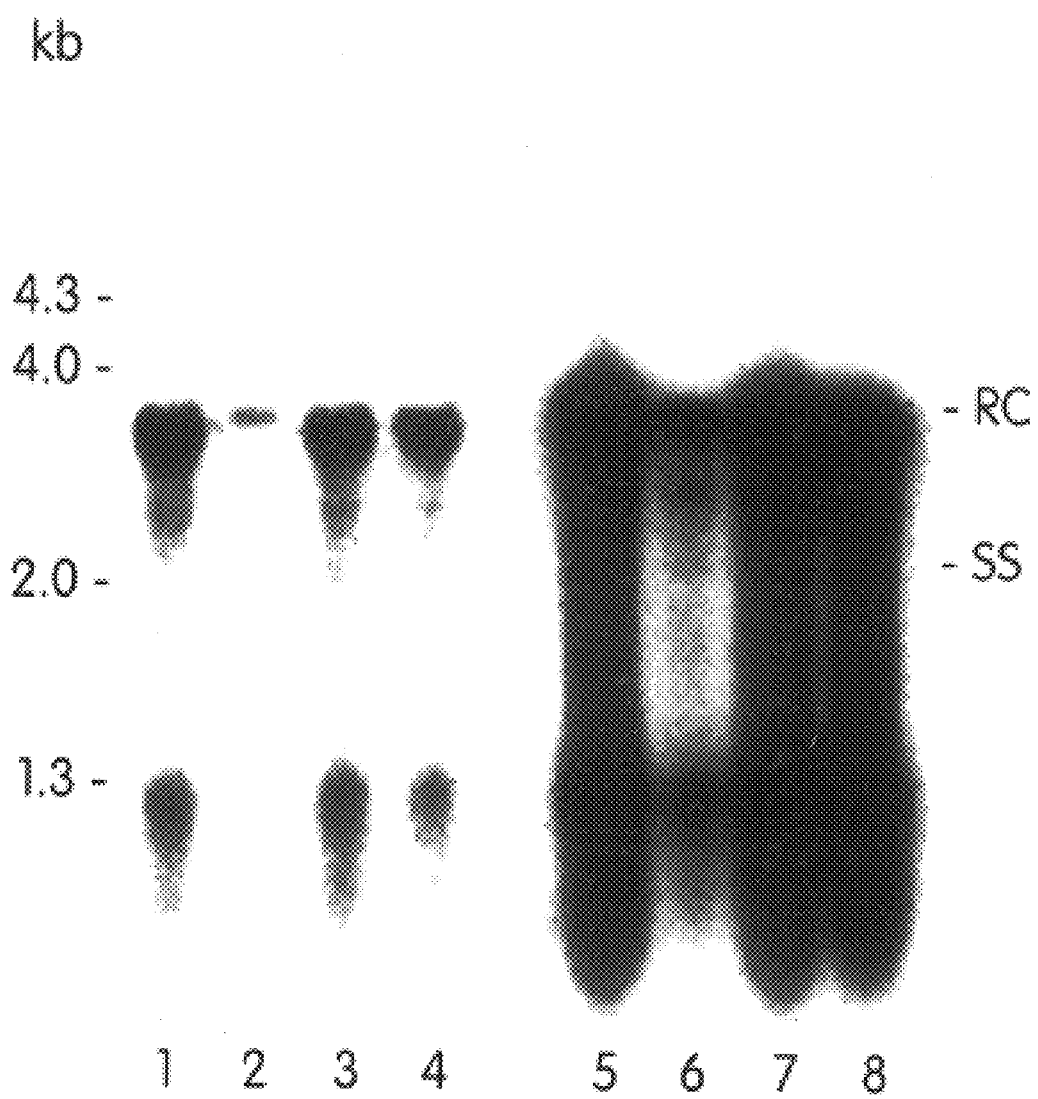
FIG. 3 shows Southern blots of DNA extracted from medium and cells after 24 hrs of exposure to antisense DNA.

Finally, in order to determine whether viral replication was affected, DNA was extracted from the medium and cells layers exposed to oligonucleotides for 24 hrs and analyzed by Southern blots. FIG. 3 shows Southern blots of DNA extracted from medium and cells after 24 hrs exposure to antisense DNA. Cells were incubated as described for FIG. 2 with 50 μM antisense DNA alone, or in the form of complexes as described for FIG. 2. After 24 hrs, medium was removed and DNA, extracted from the medium (Sells, M. A. et al. (1987) *Proc. Natl. Acad. Sci. USA* 84:1005–1009) and from the cell layer (Hirt, B. J. (1967) *Mol. Biol.* 26:365–371). Total cell protein was determined by calorimetric assay (Bio-Rad). DNA extracted from equal volumes of medium and from approximately equal numbers of cells were applied on an agarose gel, HBV DNA was identified by Southern blot using an EcoRI-BglII fragment of the HBV genome as a probe labeled with $^{32}$P and exposed to x-ray film (Sambrook, J. et al. (1989) *Molecular Cloning—A Laboratory Manual*, Cold Spring Harbor Laboratory, 2nd ed., vol. 2, pp. 10.14–10.15). Relative quantitation was achieved by densitometry and confirmed by scintillation counting of corresponding bands, normalized to equal volume or cell number, for media and cell layers, respectively. Duplicate blots were performed, a representative of which is shown above. Lanes 1–4, cell lysates; lanes 5–8, media; lanes 1 and 5, untreated controls; lanes 2 and 6, treated with complexed antisense DNA; lanes 3 and 7, treated with complexed random DNA and lanes 4 and 8, treated with antisense DNA alone. Expected positions for relaxed circular (RC) and single stranded (SS) forms are indicated on the right.

FIG. 3 lanes 1 and 5 show that untreated cells produced bands at positions expected for relaxed circular and single-stranded linear viral replicative DNA forms. Other minor bands are present, at 2.3 kb for example, as described previously for this cell line (Sells, M. A. et al. (1987) *Proc. Natl. Acad. Sci. USA* 84:1005–1009). Lanes 2 and 6 show that treatment of cells with complexed antisense DNA decreased the amount of all viral DNA forms in the medium by approximately 80% compared to untreated cells (lanes 1 and 5). Complexed random DNA, lanes 3 and 7, had no detectable effect on the levels of HBV DNA under identical conditions. Antisense DNA alone, lanes 4 and 8, decreased HBV DNA by approximately 30% relative to untreated controls. The number of viable cells as determined by trypan blue exclusion was not affected by treatment with any form of DNA (data not shown).

It has been shown previously that many cell-types are capable of taking up free oligonucleotides (Loke, S. L. et al. (1989) *Proc. Natl. Acad. Sci. USA* 86:3474–3478). Loke et al. showed that the rates of uptake were inversely proportional to the size of the oligonucleotide (Loke, S. L. et al. (1989) *Proc. Natl. Acad. Sci. USA* 86:3474–3478). However, in general, the longer the DNA sequence, the greater the specificity for target mRNA molecules. These conflicting properties illustrate two common problems with the current use of antisense oligonucleotides: inefficient uptake and lack of cell specificity. In order to improve uptake of antisense oligonucleotides, Lemaitre et al. covalently coupled an oligonucleotide to polylysine (Lemaitre, M. et al. (1987) *Proc. Natl. Acad. Sci. USA* 84:648–652) and obtained antiviral effects at several-fold lower concentrations than could be obtained with free DNA. However, the delivery was not cell-specific. Our uptake data indicate that not only can transport of oligonucleotides into cells be greatly enhanced, but the uptake can also be directed to specific cells mediated by an asialoglycoprotein-based DNA-carrier system.

Because of the specificity of DNA hybridization with mRNA to form hybrids implicated in antisense-mediated inhibition of translation, antisense oligonucleotides have been used successfully to study normal gene expression in vitro (Bevilaqua, A. et al. (1988) *Proc. Natl. Acad. Sci. USA* 85:831–835). For similar reasons, antisense oligonucleotides have also been examined previously for anti-viral effects (Goodchild, J. et al. (1988) *Proc. Natl. Acad. Sci. USA* 85:5507–5511 and Agrawal, S. et al. (1989) *Proc. Natl. Acad. Sci. USA* 86:7790–7794). For example, Agrawal et al. administered infectious virus (HIV) together with antisense oligonucleotides in a non-targeted manner to cell media (Agrawal, S. et al. (1989) *Proc. Natl. Acad. Sci. USA* 86:7790–7794). Specific inhibition of viral replication was demonstrated. Similarly, Lemaitre et al. studied a model of acute viral infection in which antisense was pre-administered to cells (Lemaitre, M. et al. (1987) *Proc. Natl. Acad. Sci. USA* 84:648–652) with substantial specific antiviral effects. Our experiments differ from these previous studies in that our cells had a pre-existing, stable viral infection with viral production maintained by an integrated viral genome. Our data indicate that although a stable infection existed, delivery of antisense oligonucleotides can dramatically inhibit viral gene expression in a specific manner. However, in vivo, persistent production of hepatitis B virus is usually due to the presence of unintegrated viral DNA (Shafritz, D. et al. (1981) *N. Eng. J. Med.* 305:1067–1073). Integration of the viral genome into that of the host is usually associated with a cessation of production of complete viral particles (Ganem, D. (1982) *Rev. Infect. Dis.* 4:1026). Whether targeted antisense delivery can be effective in the presence of an infection generated by unintegrated viral DNA remains to be seen. However, asialoglycoprotein uptake in hepatitis virus-infected HepG2 cells was found to be not substantially different from non-infected HepG2 cells (data not shown), indicating that infection by the virus did not alter the receptor activity in these cells. This suggests that targeted delivery of antisense oligonucleotides may be generally applicable to naturally infected hepatocytes, that are otherwise normal, via asialoglycoprotein receptors.

It should be noted that the oligonucleotides used in this current work were linked together by phosphorothioate bonds. These linkages are less susceptible to nuclease degradation than normal phosphodiester bonds. However, an antisense oligonucleotide synthesized with phosphodiester linkages was also effective. In addition, a variety of other synthetic strategies have been developed to confer nuclease resistance to antisense oligonucleotides (Miller, P. S. et al. (1985) *Nucleosides Nucleotides* 6:769–776). Forms that retain polyanionic character may also be deliverable by a receptor-mediated carrier system to provide enhanced and prolonged efficacy in a targeted manner.

Uptake of AsOR-Poly L-lysine-oligoDNA Complexes in Vivo

To determine whether the AsOR-poly-L-lysineoligoDNA complexes retained their ability to be recognized by hepatocyte asialoglycoprotein receptors in vivo, rats 200–250 g, were injected intravenously via a tail vein with AsOR-poly-L-lysine-[$^{32}$P]-oligoDNA alone or together with a 1000-fold molar excess of asialoorosomucoid in 0.15 M sterile saline. After 10 min, animals were killed and samples of blood, liver, spleen, lung and kidney were obtained. Tissue samples were weighed, homogenized, mixed with aqueous counting scintillant and counted for $^{32}$P radioactivity on a beta-counter. The uptake of radioactivity by each organ was expressed as the mean of the percent of the total injected counts. These data indicate that complexed single-stranded (antisense) oligoDNA sequences can be targeted specifically to the liver by simple intravenous injection.

Organ Distribution of $^{32}$P-(oligonucleotide) DNA as an AsOR-PL Complex

| | % injected |
|---|---|
| Blood | 6.0 |
| Heart | 2.1 |
| Lung | 4.5 |
| Kidney | 2.7 |
| Spleen | 3.7 |
| Liver | 81 |

Competition with 1000-fold Molar Excess Cold AsOR

| | % injected |
|---|---|
| Blood | 74.1 |
| Heart | 1.5 |
| Lung | 3.2 |
| Kidney | 4.1 |
| Spleen | 3 |
| Liver | 14.1 |

EXAMPLE 2

MATERIALS AND METHODS

ASSAYS FOR DETERMINING THE EFFECT OF AsOR-PL-α1(I) PROCOLLAGEN ANTISENSE DNA ON PROCOLLAGEN BIOSYNTHESIS

Cell Culture and Treatment

A mouse fibroblast cell line (3T3-AsGR) producing collagen and stably transfected with the asialoglycoprotein (AsG) receptor genes kindly provided by Dr. Michael Shia (Massachusetts Institute of Technology, Cambridge, Mass.) was grown in DMEM and 10% FBS. Confluent 35 mm dishes of 3T3-AsGR were treated with α1(I) antisense DNA alone (1.3 μM or 2.7 μM) or varying concentrations of antisense DNA complex (1.3 μM, 1.7 μM, or 2.7 μM antisense) for 12–16 hours (overnight) at 37° C. in DMEM and 10% FBS. The medium was removed and replaced with labeling medium containing 5 μCi/ml of [$^3$H]-proline, 50 μg/ml L-ascorbate and varying concentrations of antisense DNA or complexes. Cells were incubated for 4 hours at 37° C. in the labeling medium. Newly synthesized procollagens and other proteins were determined by bacterial collagenase digestion (Peterkofsky, B. and Diegelmann, *Biochemistry* 10:988–994 (1971)).

Collagenase Digestion

The labeling medium was removed and set aside.

Buffer containing protease inhibitors (0.5 M Tris, pH 7.4, 0.4 mM NEM, 0.2 mM PMSF, 2.5 mM EDTA) was added to the cell layer and the cell layer was removed and pooled with the supernatant. The entire mixture was homogenized using a Dounce homogenizer and ice cold TCA was added to a final concentration of 15%. TCA precipitable proteins were digested with bacterial collagenase (Form III, Advanced Biofactures, Lynbrook, NY) at 37° C. for 2 hours followed by precipitation with TCA-tannic acid. The collagenase-sensitive radioactivity in the supernatant was separated by centrifugation to measure newly synthesized procollagen production. The collagenase-resistant precipitated radioactivity was used to calculate non-collagenous protein production. All assays were normalized to equal numbers of cells.

Preparation of Taraetable Antisense DNA

A targetable, soluble DNA carrier was prepared by coupling asialoorosomucoid to poly L-lysine (Sigma) ($M_r$=41, 000) using 1-ethyl-3-(3-dimethyl-aminopropyl) carbodiimide) (Pierce) as described previously (Wu, G. Y. and Wu, C. H. (1987) *J. Biol. Chem.* 262:4429–4432) except that the conjugate was purified by cation exchange chromatography using a high pressure liquid chromatographic system (Rainin) employing an Aquapore C-300 column (Rainin) and stepwise elution with 0.1 M sodium acetate, pH 5.0, 2.5, 2.25 and 2.0. The second peak eluted from the column, as detected by U.V. absorption at 230 nm, was determined to be the optimal conjugate form and was used for all subsequent experiments. A 24-mer oligodeoxynucleotide, complementary to the 5'-region of the pro α1 procollagen mRNA (See SEQUENCE ID NO. 2-CCGGAGGTCCACAAAGCTGAACAT) was synthesized with phosphodiester linkages on an automated nucleotide synthesizer (Applied Biosystems) (Matsukura, M. et al. (1987) *Proc. Natl. Acad. Sci. USA* 84:7705–7710). Specifically, this sequence is antisense to the first 24 nucleotides of pro ml procollagen beginning at the α1(I) translation start site and including a portion of the first intron. The purity of oligonucleotides was determined by electrophoresis through 15% polyacrylamide gels stained with ethidium bromide. Antisense DNA was titrated with conjugate to form a soluble complex using an agarose gel retardation system as described previously (Wu, G. Y. and Wu, C. H. (1987) *J. Biol. Chem.* 262:4429–4432) and a conjugate to DNA ratio of 2:1 by weight (asialoorosomucoid-polylysine (AsOR-PL): DNA) was selected.

Assay for Receptor-Mediated Uptake of Complexed Antisense DNA

In order to characterize the uptake capacity of the asialoglycoprotein receptors on the 3T3-AsGR cells, confluent 35mm dishes of 3T3-AsGR cells in DMEM and 10% FBS were stripped with phosphate buffered saline (PBS)-10 mM EDTA, pH 5.0 and incubated with 2 μg/ml [$^{125}$I]-AsOR with specific activity of 1×10$^6$ cpm/μg. Uptake was determined as described previously for asialoglycoproteins (Schwartz, A. L. et al. (1981) *J. Biol. Chem.* 256:8878–8881). In brief, cells were incubated with [$^{125}$I]-AsOR at 37° C. and at regular time intervals (0.5, 1, 2, or 4 hours), dishes were chilled to 4° C., washed three times with cold 10 mM EDTA-phosphate buffered saline and the cell layers solubilized with 0.1 NaOH and gamma counted. This process was repeated by incubating the 3T3-AsGR cells with [$^{32}$P]-DNA-AsOR-PL (1.3 μM antisense) or 1.3 μM DNA-[$^{125}$I]-AsOR-PL (specific activity=0.5×10$^6$ cpm/μg) to determine the rate of uptake of antisense complex except that cell layers incubated with $^{32}$P-labeled complex were scintillation counted. Parallel dishes were incubated with the radiolabeled ligand together with a 300-fold weight excess of cold AsOR to determine non-specific uptake. To ascertain counts bound to the cell surface, identical sets of cells were incubated at 4° C. with ligands and, after washing as described above, the cell layers were removed and adherent radioactivity was determined by scintillation counting. Uptake was calculated as the difference between total cell-associated counts at 37° C. and counts bound to the cells at 4° C. for each time point.

RNA Extraction and RNA Dot Blots

Confluent 10 cm dishes of 3T3-AsGR cells in DMEM and 10% FBS were incubated overnight at 37° C. with one or a combination of the following: (1) α1(I) antisense oligonucleotide (1.3 μM or 2.7 μM); (2) similar concentrations of antisense complexed with AsOR-PL. Total cellular mRNA was extracted by the guanidinium thiocyanate method. (Chomczynski, P. and Sacchi, N., *Anal. Biochem.* 162: 156–159 (1987)). Quantity and quality of the extracted RNA were determined by $A^{260}/A^{280}$ absorbance and ethidium bromide stained formaldehyde gels.

Dot blot studies starting with 20 μg of total RNA were serially diluted 2-fold in 20× SSC pH 7.0. Samples were heat-denatured in 50% formamide, 7% formaldehyde, and 1× SSC pH 7.0 (Sambrook, J., et al. *Molecular Cloning* 7.54, 1989). Samples were applied to nitrocellulose filters using slot blot apparatus, cross-linked to the filter by ultraviolet exposure, and prehybridized for 3 hours at 42° C. The cDNA probes, labeled with $^{32}P$ using a random priming method (Sambrook, J., et al. *Molecular Cloning* 13.44, (1989)) were rat proα1(I) and β-actin, both linearized with EcoRI, and a 900bp piece of rat proα2(I) The nitrocellulose filters were hybridized with the probes ($0.5-1.0 \times 10^7$ cpm/filter) overnight at 42° C., washed, and exposed to film. Quantitation was done by scintillation counting of the filters.

Northern Blots

Total RNA samples (60 μg) were heat denatured in 50% formamide, 2× formaldehyde running buffer, 7% formaldehyde at 55° C. for 15 minutes (Sambrook, J., et al. *Molecular Cloning* 7.43, (1989)). Samples were run on formaldehyde gels (1% agarose, 2.2 M formaldehyde) for 4 hours at 100 mvolts on ice. Molecular weight and control RNAs were stained in 0.1 ammonium acetate and 0.5 μg/ml ethidium bromide and photographed with a fluorescent ruler. The remaining gel was washed several times with water, the RNA hydrolyzed with 0.5 N NaOH for 20 minutes, and soaked in 20× SSC for 45 minutes. The RNA was transferred onto a nitrocellulose filter under vacuum for one hour and cross-linked to the filter by exposure to ultraviolet irradiation using a Stratalinker. Conditions for prehybridization and hybridization were the same as in the slot blot studies.

RESULTS

Characterization of 3T3-AsGR Cells

Since the 3T3-AsGR cells do not normally possess asialoglycoprotein receptors, they were transfected with the asialoglycoprotein receptor genes and were found to have a $K_d$ of $1.5 \times 10^{-9}$ M, a binding saturation with [$^{125}I$]-AsOR at 1.8 μg/ml, and an uptake rate of [$^{125}I$]-AsOR of 1.8 pmole/million cells/hr. The number of asialoglycoprotein receptors per cell was 250,000.

The 3T3-AsGR cells displayed a linear uptake of α1(I) antisense DNA-AsOR-PL complex up to 4 hours at a rate of 18.2 pmole of DNA/million cells/hr. In contrast, the rate of uptake of labeled α1(I) antisense DNA alone was 0.15 pmole DNA/million cells/hr. Uptake of AsOR in a 300× excess by weight competed with the uptake of α1(I) antisense DNA complex.

Effect of α1(I) Antisense DNA Complex on Collagen Synthesis

α1(I) antisense DNA complexes inhibited collagen production by 3T3-AsGR cells. This inhibition was specific for collagen production and was dependent on the concentration of α1(I) antisense DNA in the complex. This result is set forth in the following table.

| μM α1(I) | collagen proteins | noncollagen proteins | collagen production (% control) |
|---|---|---|---|
| | cpm/million cells | | |
| 0 | 4,330 | 45,000 | 100 |
| 1.3 | 3,190 | 44,500 | 74 |
| 1.7 | 2,770 | 45,660 | 64 |
| 2.7 | 2,210 | 40,500 | 56 |

Effect of α1(I) Antisense DNA Complex on Procollagen I mRNA Levels

α1(I) antisense DNA complex specifically inhibited mRNA of the α1(I) chain. But at a higher concentration (2.7 μM) of antisense DNA complex, mRNA of both the α1(I) and α2(I) chain was inhibited. The following table is a result of the quantitation of several dot blot analyses.

| μM | pα1(I) | pα2(I) | β-actin |
|---|---|---|---|
| | (% control) | | |
| 0 | 100 | 100 | 100 |
| 1.3 | 71 | 100 | 102 |
| 2.7 | 65 | 85 | 106 |

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. A soluble molecular complex comprising a single-stranded antisense oligonucleotide which hybridizes to an RNA in a target cell, said antisense oligonucleotide complexed with a carrier comprised of a ligand for the asialoglycoprotein receptor and a polycation.

2. A soluble molecular complex of claim 1, wherein the RNA comprises cellular or viral RNA.

3. A soluble molecular complex of claim 2, wherein the RNA comprises hepatitis viral RNA.

4. A soluble molecular complex of claim 3, wherein the RNA comprises a hepatitis RNA polyadenylation site.

5. A soluble molecular complex of claim 1, wherein the RNA comprises a transcript from an oncogene.

6. A soluble molecular complex of claim 1, wherein the polycation is polylysine.

7. A soluble molecular complex of claim 1, wherein the target cell is an hepatocyte.

8. A soluble molecular complex of claim 1, wherein the ligand is an asialoglycoprotein.

9. A composition comprising the molecular complex of claim 1 and a physiologically acceptable vehicle.

10. A soluble molecular complex comprising an antisense DNA which hybridizes to a complementary RNA in a target cell, said antisense DNA noncovalently complexed with a carrier comprised of a ligand for the asialoglycoprotein receptor and a polycation.

11. A method of delivering a single stranded antisense oligonucleotide to an asialoglycoprotein receptor-bearing cell in a mammal, comprising administering to the mammal a soluble molecular complex comprising a single-stranded antisense oligonucleotide which hybridizes to a complementary RNA in the asialoglycoprotein receptor-bearing cell, said antisense oligonucleotide complexed with a carrier comprised of a ligand for the asialoglycoprotein receptor and a polycation, such that the antisense oligonucleotide is delivered to the asialoglycoprotein receptor-bearing cell.

12. A method of claim 11, wherein the RNA comprises a viral RNA transcript.

13. A method of claim 12, wherein the RNA comprises a hepatitis viral RNA transcript.

14. A method of claim 13, wherein the RNA comprises a hepatitis viral RNA polyadenylation site.

15. A method of claim 11, wherein the polycation is polylysine.

16. A method of claim 11, wherein the asialoglycoprotein receptor-bearing cell is an hepatocyte.

17. A method of claim 16, wherein the ligand is an asialoglycoprotein.

18. A method of claim 11, wherein the molecular complex is administered intravenously.

19. A method of delivering a single stranded antisense oligonucleotide to an asialoglycoprotein receptor-bearing cell comprising contacting the cell with a molecular complex comprising an antisense oligonucleotide which hybridizes to a complementary RNA in the cell, said antisense oligonucleotide complexed with a carrier comprised of a ligand for the asialoglycoprotein receptor and a polycation, such that the antisense oligonucleotide is delivered to the asialoglycoprotein receptor-bearing cell.

20. A method of claim 19, wherein the polycation is polylysine.

21. A method of claim 19, wherein the molecular complex is administered intravenously.

22. A method of inhibiting gene expression by an RNA in a cell comprising contacting the cell with a molecular complex comprising an antisense oligonucleotide which hybridizes to the RNA in the cell, said antisense oligonucleotide complexed with a polycationic carrier comprised of a ligand for the asialoglycoprotein receptor and a polycation, so that the antisense oligonucleotide is delivered to the cell and inhibits gene expression by the RNA.

23. A method of claim 22, wherein the RNA comprises cellular or viral RNA.

24. A method of claim 22, wherein the polycationic carrier comprises polylysine.

25. A method of claim 22, wherein the molecular complex is administered intravenously.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 21 nucleotides
      (B) TYPE: nucleic acid
      (C) STRANDEDNESS: single
      (D) TOPOLOGY: linear (ii) MOLECULE TYPE: DNA (iv) ANTI-SENSE: yes (ix) FEATURE: Complement to hepatitis B
        virus polyadenylation site (xi) SEQUENCE DESCRIPTION: SEQ ID NO:1:

-continued

```
TTTATAAGGG TCGATGTCCA T                                              21

(2) INFORMATION FOR SEQ ID NO:2:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: DNA (iv) ANTI-SENSE: yes (ix) FEATURE: Complement to first 24 nucleotides of pro a1
            procollagen beginning at the a1(I) translation
            start site and including a portion of the first
            intron.

(xi) SEQUENCE DESCRIPTION: SEQ ID NO:2:

CCGGAGGTCC ACAAAGCTGA ACAT                                           24
```